US010695560B2

(12) United States Patent
Wang

(10) Patent No.: US 10,695,560 B2
(45) Date of Patent: Jun. 30, 2020

(54) PHYSICAL THERAPY DEVICE FOR PETS

(71) Applicant: Chien-Chi Wang, Taipei (TW)

(72) Inventor: Chien-Chi Wang, Taipei (TW)

( * ) Notice: Subject to any disclaimer, the term of this patent is extended or adjusted under 35 U.S.C. 154(b) by 87 days.

(21) Appl. No.: 16/120,409

(22) Filed: Sep. 3, 2018

(65) Prior Publication Data

US 2020/0069936 A1   Mar. 5, 2020

(51) Int. Cl.
| | | |
|---|---|---|
| *A61N 1/00* | (2006.01) | |
| *A61N 1/26* | (2006.01) | |
| *A61F 7/00* | (2006.01) | |
| *A61H 23/02* | (2006.01) | |
| *A61N 1/28* | (2006.01) | |
| *A61D 99/00* | (2006.01) | |
| *A61D 7/00* | (2006.01) | |

(52) U.S. Cl.
CPC .............. *A61N 1/26* (2013.01); *A61D 7/00* (2013.01); *A61D 99/00* (2013.01); *A61F 7/00* (2013.01); *A61H 23/02* (2013.01); *A61N 1/28* (2013.01); *A61F 2007/0086* (2013.01); *A61H 2201/102* (2013.01); *A61H 2201/1692* (2013.01); *A61H 2203/03* (2013.01)

(58) Field of Classification Search
CPC ... A61N 1/26; A61N 1/28; A61D 7/00; A61D 99/00; A61F 7/00; A61F 2007/0086; A61H 23/02; A61H 2201/102; A61H 2201/1692; A61H 2203/03
See application file for complete search history.

(56) References Cited

U.S. PATENT DOCUMENTS

| | | | | |
|---|---|---|---|---|
| 5,183,006 A | * | 2/1993 | Robinson | A01K 13/003 119/603 |
| 8,088,086 B1 | * | 1/2012 | Schmuck | A61H 7/004 601/84 |
| 8,784,384 B2 | * | 7/2014 | Boyden | A61M 37/0015 604/173 |
| 2002/0026226 A1 | | 2/2002 | Ein | |
| 2007/0106341 A1 | | 5/2007 | Moss et al. | |
| 2009/0287284 A1 | * | 11/2009 | Soong | A61N 1/0452 607/115 |
| 2012/0265274 A1 | * | 10/2012 | Gomez De Diego | A61N 5/0617 607/89 |
| 2013/0296745 A1 | * | 11/2013 | Cheatham, II | A61H 23/00 601/18 |
| 2017/0367923 A1 | * | 12/2017 | Bergbacka | A01K 13/002 |
| 2018/0014633 A1 | * | 1/2018 | Davidov | A23L 2/70 |
| 2018/0015299 A1 | * | 1/2018 | Kawa | A61N 5/0617 |

* cited by examiner

*Primary Examiner* — Steven O Douglas

(57) ABSTRACT

A physical therapy device for pets contains: a current output unit, a comb body, and a conductive platform. The current output unit is electrically connected to a power to supply an output current and control a current value of the output current. The comb body includes a first terminal and a second terminal, a side of the first terminal has a first brushes which are made of a plurality of conductive materials. The first terminal is separately electrically connected to the current output unit, and the second terminal is held by a user. The conductive platform is electrically connected to the current output unit so that the current output unit outputs the current to the pets via the first brushes.

20 Claims, 9 Drawing Sheets

PHYSICAL THERAPY DEVICE FOR PETS

BACKGROUND OF THE INVENTION

1. Field of the Invention

The present invention generally relates to a physical therapy device, and more particularly to the physical therapy device for pets.

2. Description of the Prior Art

The physical therapy (thereinafter PT) mainly utilities the methods of light, electric, water, chill, heat and so on to prevent, cure, and deal with the injures in the body because of diseases and external forces. The present PT terms include the light therapy such as ultraviolet, the electrotherapy such as the electrical stimulation, the water therapy such as the water exercise, the cryotherapy such as the ice pack, the heat therapy such as the hot pack, the force therapy such as massage, and the exercise therapy such as the muscle training.

Wherein, the electrical stimulation in the electrotherapy mainly pastes the two electrode sheets to the patient departments such as the waist, and then supplies the current to the electrode sheets by an electrotherapy equipment so as to the electrotherapy equipment, the two electrode sheets and the body form a conductive circuit together. When the current passes through the body, it stimulates nerves, alternatively promotes the muscles to contract and relax to treat the patient departments.

Not only the human body has the problems mentioned above, but also the pet body does. That is, the pets will be injured since the external force or be ageing. It can be treated by the electrotherapy to cure and relax the pain on the body. However, in the contrast between the body of the pet and the human, there are much hair on the skin surface of the pet body so that on which the electrode sheets are difficult to be pasted. Therefore, the electrotherapy is not effective.

To improve the problems mentioned above, the invention provides a means so that the pets can be treated by the electrotherapy to cure the pains on the body.

SUMMARY OF THE INVENTION

In view of the foregoing, a physical therapy device for pets of the present invention is applicable for and contains: a current output unit electrically connected to a power to supply an output current and control a current value of the output current, a comb body that includes a first terminal and a second terminal, wherein a side of the first terminal has multiple first brushes made of a plurality of conductive materials and separately electrically connected to the current output unit, the second terminal is configured to be held by a user, and a conductive platform electrically connected to the current output unit so that the current output unit outputs the current to the pets via the multiple first brushes.

The primary aspect of the present invention is to provide a physical therapy for the pets by which the pets lie on the conductive platform and a user grooms the hairs of the pets by using the comb body so as to contact the skins of the pets by multiple first brushes. In the meantime, when the current output unit outputs the current, the current output unit, the first brushes, the pets, and the conductive platform will form the conductive circuit to treat the pets by the physical therapy.

DETAILED DESCRIPTION OF THE INVENTION

The traditional electrotherapy treaded on the human body mostly utilizes the positive and the negative electrode sheet (to be pasted on the skin of the body), the positive and the negative clamps (maybe clamp the fingers or ears and so on) but the pets cannot do as the same as the human because of their hair on the skin. For the purposes, the inventor designs the means of PT for pets. The below descriptions explain with the contexts and the diagrams so that the examiners can completely comprehend the advantages, characteristics, features of the application, which relates to a physical therapy device for pets.

Figure 7:
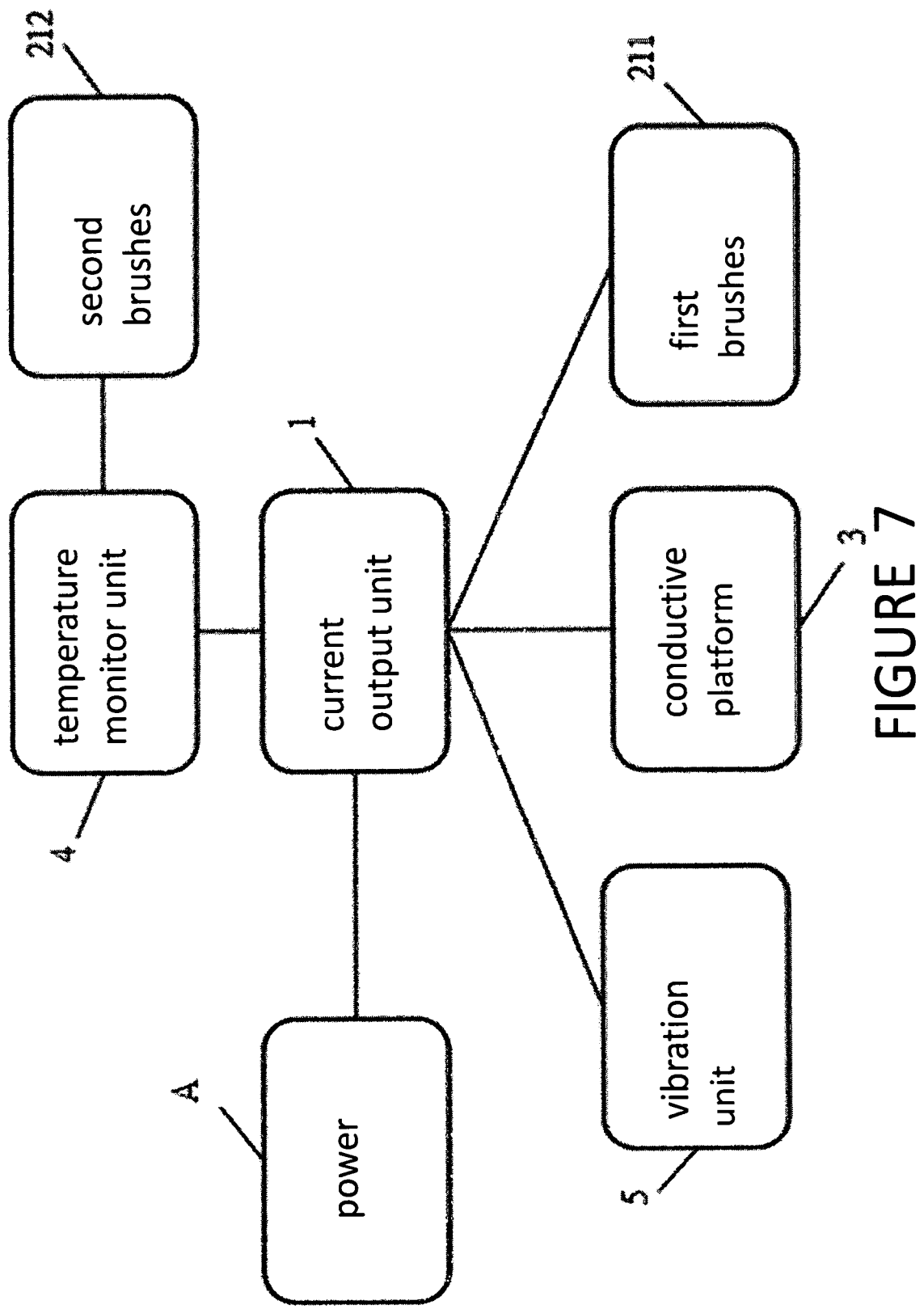
FIG. 7 illustrates the electrical links of the members of the schematic diagram of the present invention.

A Current Output Unit (1):

Referring to FIG. 7, the current output unit (1) is electrically connected to a power to supply an output current and to control the value of the current. Therefore, the output current of the current output unit (1) is adjusted by a user to provide varieties of the degrees of the electrotherapy.

Figure 1:
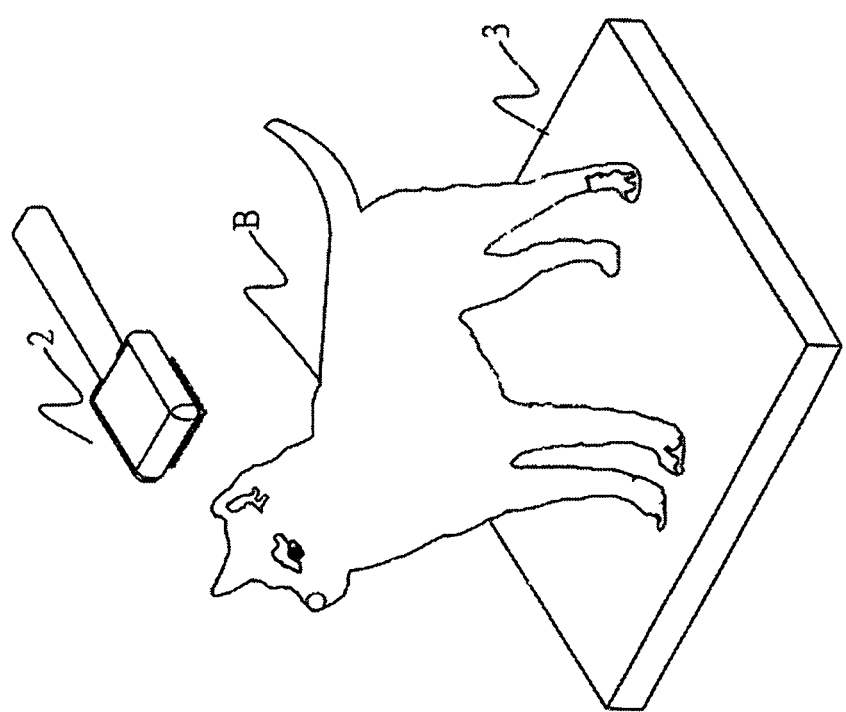
FIG. 1 illustrates an appearance and a using state schematic diagram of the present invention.
Figure 2:
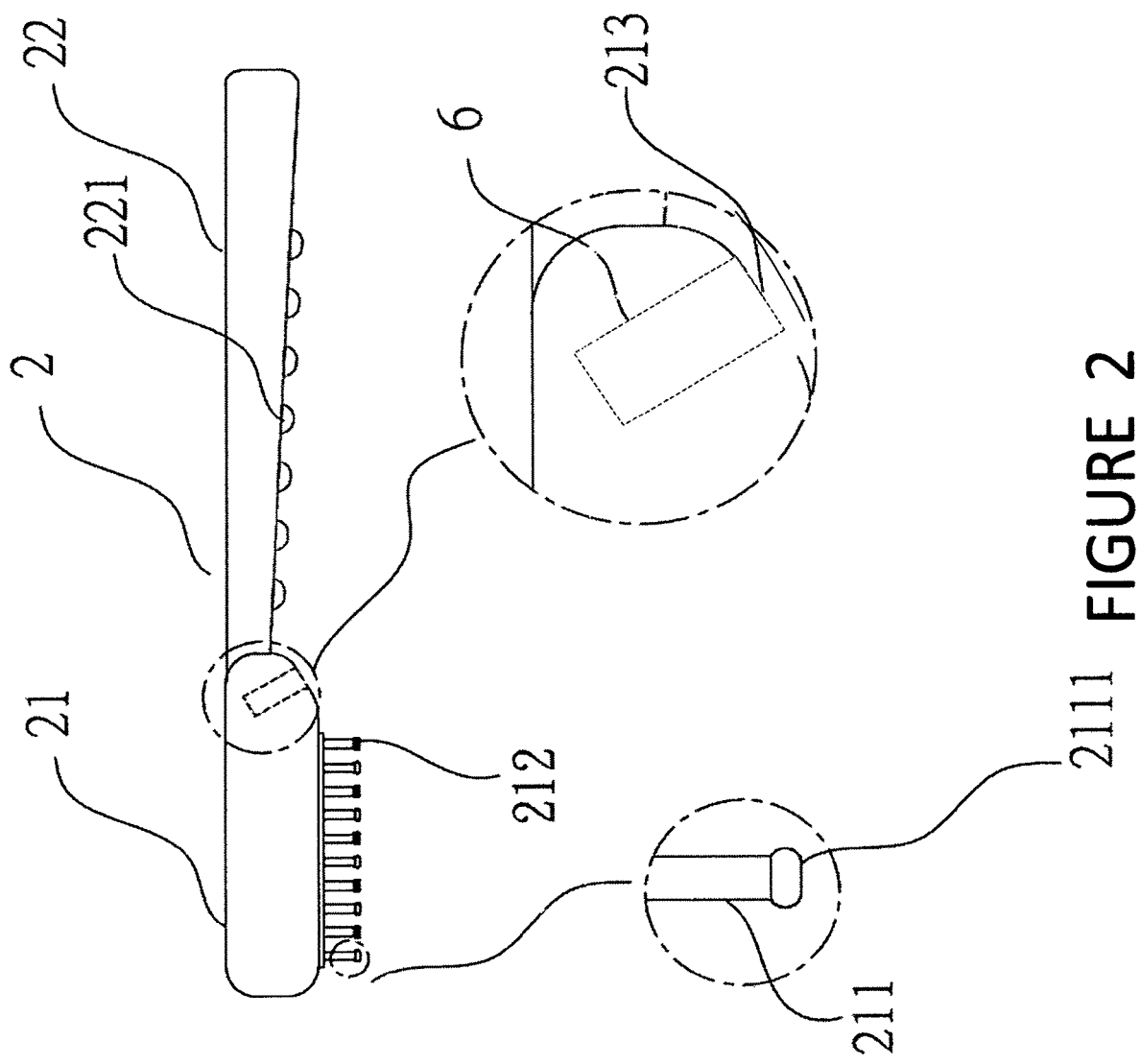
FIG. 2 illustrates the side view of the comb body and the embodiment of the schematic diagram of the present invention.

A Comb Body (2):

Referring to the FIGS. 1, 2, and 7, the aspect and the contour of the comb body (2) are not limited to the figures, but anything applicable for the comb body (2) is the scope of the invention. The comb body (2) has a first terminal (21) and a second terminal (22). The side of the first terminal (21) has multiple first brushes (211) made of a plurality of conductive materials and separately electrically connected to the current output unit (1). The second terminal (22) is configured to be held by the user. Accordingly, when the current output unit (1) supplies the output current continuously, the output current is carried to the pets (B) by the first brushes (211) so as to perform the electrotherapy.

A Conductive Platform (3):

Referring to FIGS. 1 and 7, the conductive platform (3) is electrically connected to the current output unit (1). The conductive platform (3) is used as a platform on which the pets (B) lie so that the current output unit (1) outputs the current, and the first brushes (211), the conductive platform (3) and pets (B) form a conductive circuit together. The conductive platform (3) is not limited to the specification. For example, the conductive platform (3) includes a conductive rubber blanket pad, a metal platform, a pets operating table or anything which is conducted electricity to form the conductive circuit mentioned above and is used as a platform on which the pets (B) lies is the scope of the present invention.

Accordingly, as shown in FIGS. 1, 2 and 7, it mainly utilizes the method of the electrical stimulation to treat the pets (B). The pets (B) have much and long hairs; therefore, the hairs easily affect the conductive efforts. When the pet (B) lies on the conductive platform (3), the current output unit (1) is active (enables). Therefore, while the user grooms the pet, the current output unit (1), the first brushes (211), the conductive platform (3), and the pet (B) form the conductive circuit together so as to treat the pet (B) by the electrotherapy. The whole process is peaceful and smooth; therefore, the pet (B) does not repel excessively. Furthermore, the conductive silicones (2111) separately formed in the terminal of the first brushes (211) not only have the effects in the electric therapy, but also message acupuncture points so as to avoid the pets feeling uncomfortable because of the thorns of the terminal of the first brushes (211).

In addition, referring to FIGS. 1, 3, and 7 again, the physical therapy device of the present invention provides the cryotherapy and the heat therapy, wherein the effects of the physical therapy device include an active mode and a passive mode. First, the passive mode is introduced as below. There is a temperature monitor unit (4) electrically connected to the current output unit (1) inside the comb body (2). The temperature monitor unit (4) is configured to set a predetermined temperature value. The side of the first terminal (21) has second brushes (212) made of a plurality of thermal conductive materials and separately connected to the temperature monitor unit (4), and the temperature monitor unit (4) is configured to maintain the second brushes (212) at the predetermined temperature value.

Figure 3:
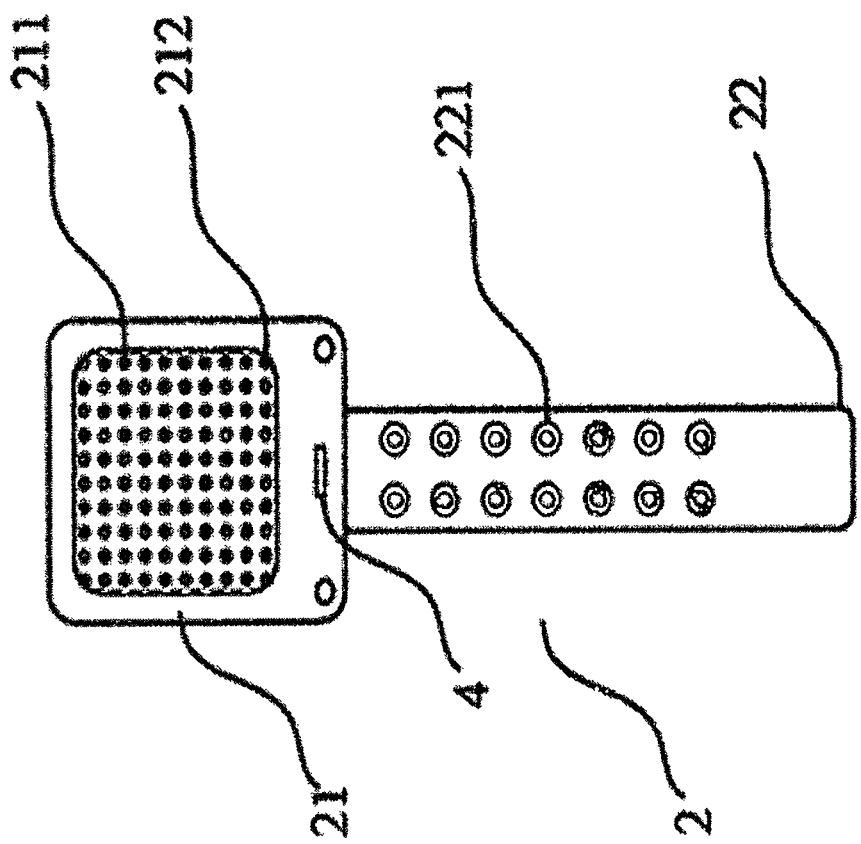
FIG. 3 illustrates the top view of the comb body and the embodiment of the schematic diagram of the present invention.

Referring to FIGS. 1, 3, and 7, the effects of the cryotherapy and the heat therapy in the passive mode depend on the temperature value of the cryotherapy and the heat therapy set by the user so as to set the predetermined temperature value. After the predetermined temperature value is set, the temperature monitor unit (4) maintains the temperature of the second brushes (212) at the predetermined temperature value. In fact, it is not essential for the pets to lie on the conductive platform (3) in the embodiment, but the pets are groomed by the user. When grooming the pets by using the first brushes (211), the temperature monitor unit (4) generates a high or low temperature for the effects of the cryotherapy and the heat therapy. When the pets lie on the conductive platform (3), the user treats the pets by the electric therapy, the cryotherapy (provide the effects of the ice therapy) and the heat therapy (provide the effects of the hot pack) of the physical therapy, thus enhancing the whole effects of the treatments.

Referring to FIG. 7, as the embodiment mentioned above, the cryotherapy and the heat therapy in the active mode are embodied as follows. The temperature monitor unit (4) senses the temperature in the peripheral environment and senses the temperatures of the pets (B) to determine the predetermined temperature value according to the results of sensing.

Accordingly, referring to FIGS. 1, 3, and 7 again, the embodiment is implemented by the active mode to set the temperature. The different with the passive mode is that the treatment contacts the skin of the pets (B), and that the temperature monitor unit (4) senses the body temperature of the pets (B) and the temperature in the peripheral environment at the meanwhile to determine the predetermined temperature value and control the temperature of the second brushes (212) so as to provide the effects of the cryotherapy and the heat therapy. As the same as the embodiment mentioned above, it is not essential for the pets (B) to lie on the surface of the conductive platform (3) to generate the effects of the cryotherapy and the heat therapy. When the pets (B) lie on the conductive platform (3), the pets (B) not only gain the electric therapy but also gain the better the treatments.

Because the pets (B) have the problems of the muscle tensions, the user needs to massage the pets. Therefore, referring to FIGS. 3, 4 and 7, the physical therapy device of the present invention is embodied by a vibration unit (5) electrically connected to the current output unit (1) and fixed inside the second terminal (22), wherein a side of the second terminal (22) has a plurality of bumps (221).

Figure 4:
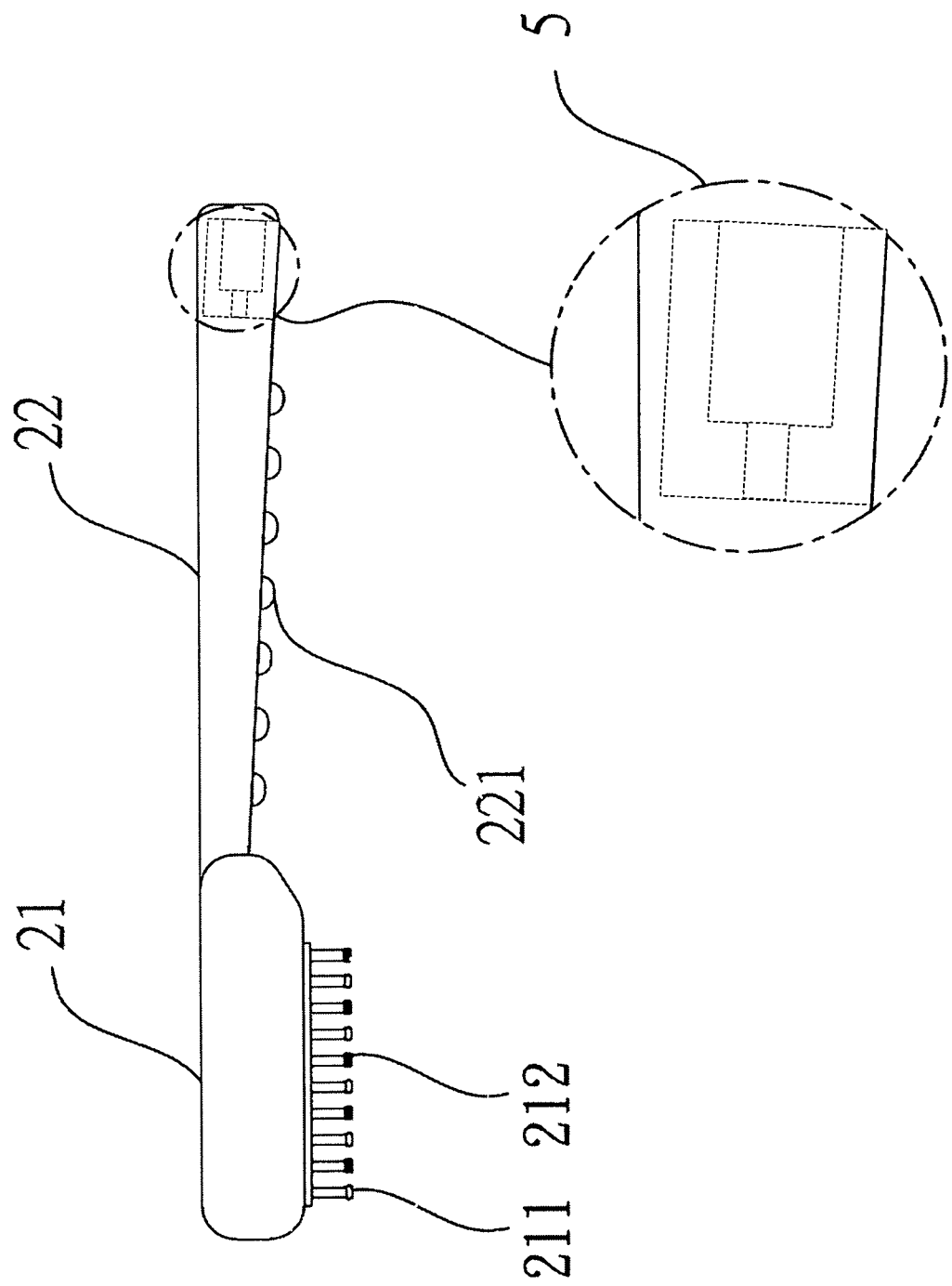
FIG. 4 illustrates the first embodiment of the comb body of the schematic diagram of the present invention.

Accordingly, as shown in FIGS. 1, 4, and 7, the physical therapy device of the present invention is not limited to lie the pets on the conductive platform (3) but anyplace, such as the legs of the user, can let the pets lie. After that, the user holds the first terminal (21) and enables the vibration unit (5) so that the bumps (221) beat and vibrate the bodies of the pets via the vibration method. It stimulates the acupuncture points and relaxes the pets (B).

In summary, the invention mainly provides the effects of the physical therapy for the pets such as the electrotherapy, the cryotherapy and the heat therapy. At the meanwhile, the physical therapy device of the present invention provides the effects of massaging and relaxing the muscles. Furthermore, the aromatherapy is widely used by the modern man; therefore, the inventor thinks that it also can be used on the pets (B) to gain the effects significantly. Accordingly, referring to FIG. 2, the physical therapy device of the present invention is implemented by an odor releasing unit (6) mounted inside the first terminal (21) and configured to release the odor. Furthermore, the surface of the first terminal (21) has a hole (213) connected to the odor releasing unit (6), as shown in FIG. 2.

Referring to FIGS. 1 and 2, the embodiment is the same as the precedent embodiment of the vibration unit (5), it is not essential to let the pets lie on the conductive platform (3). The pets only need to be fixed for grooming and to be treated by the physical therapy by the owner. At the same time, the odor releasing unit (6) releases the odor to relax and comfort the pets. Similarly, the pets (B) lie on the conductive platform (3) in the embodiment. After the current output unit (1) is enabled, the physical therapy device provides the electrotherapy, the physical therapy and the aromatherapy for the pets and gain the whole efforts of the the physical therapy device of the present invention.

Figure 5:
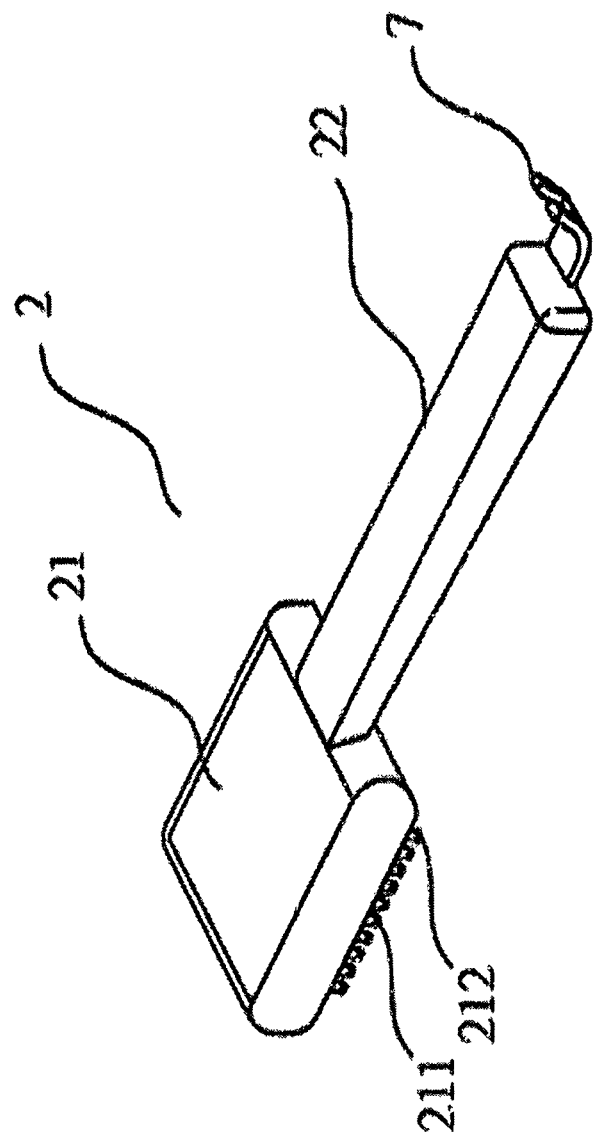
FIG. 5 illustrates the second embodiment of the comb body of the schematic diagram of the present invention.

Referring to FIG. 5, to relax the pets is not limited to the method of the vibration. It is performed by touching through the fingertips, pressing, fondling, or scratching. Accordingly, the physical therapy device of the present invention is further implemented by a massage fork (7) arranged in the end of the second terminal (22).

Referring to FIG. 5, when the embodiment is implemented, the user holds the first terminal (21) to simulate the fingers by the massage fork (7) to press, scratch, and fondle the bodies of the pets (B). Since the touching of the fondling builds the relations and relax the feelings with the pets (B), the method further gain the effects of the physical therapy. In addition, the embodiment can operate with the preceding one to enhance the effects of the massage fork (7) by the vibration unit (5) having the functions of the vibrating.

Figure 6:
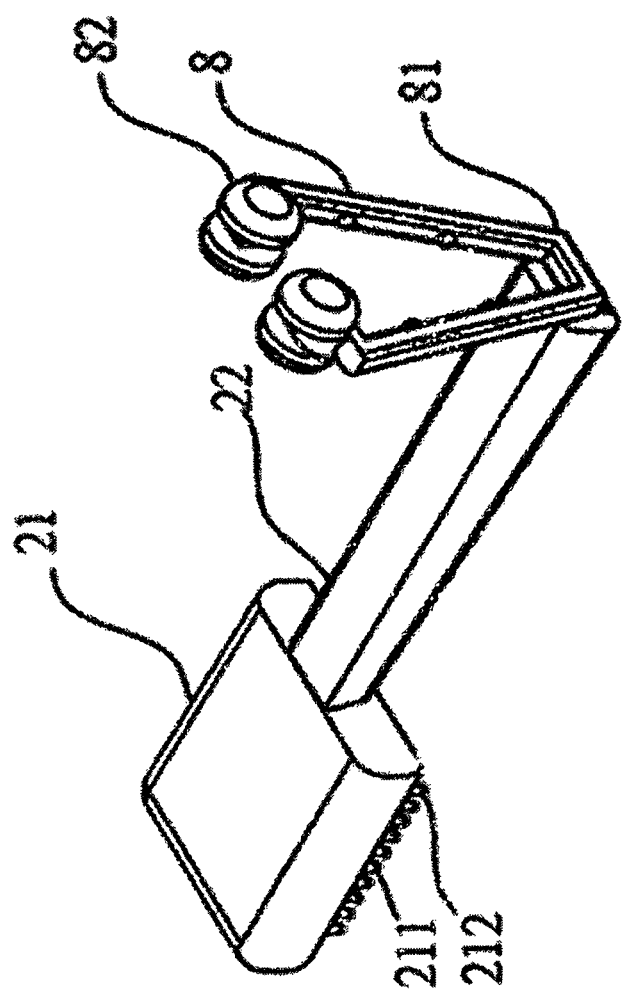
FIG. 6 illustrates the third embodiment of the comb body of the schematic diagram of the present invention.

Referring to FIG. 6, it is not limited to massage the muscles of the pets (B) by the method of the vibration. It can be performed by the rollers to roll and press the muscles for the relaxation. The embodiment includes a second massage member (8) fixed at the surface of the second terminal (212). The second massage member (8) includes clamps (81), which have the ability of the rebound to distant from each other under the external force or are close to each other under the force of the rebound. In addition, the inner portion in the two terminals of the second massage member (8) has a wheel body (82) separately.

Referring to FIG. 6, similarly, the embodiment is not essential to let the pets (B) lie on the conductive platform (3). It is performed by holding the first terminal (21) as you wish and rolling the second massage member (8) in the reciprocating motion on the bodies of the pets (B). Accordingly, the pets (B) are massaged and relaxed to achieve the physical therapy by the rolling of the wheel body (82) and the clamping force formed between the wheel body (82).

Figure 8:
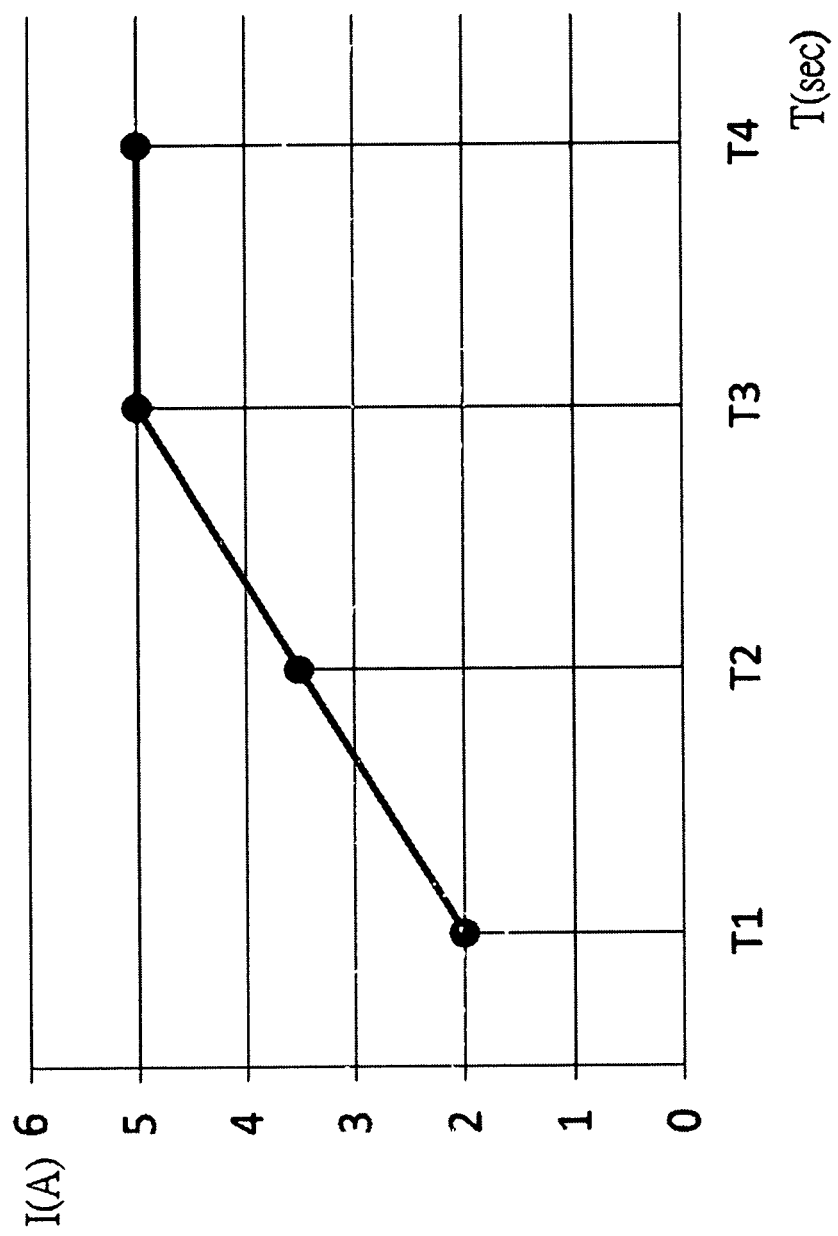
FIG. 8 illustrates the first schematic diagram of the output current of the current output unit of the present invention.

Referring to FIGS. 7 and 8, when the biology suddenly receives to the current, it will not feel comfortable. To reduce the uncomfortable feeling, the embodiment of the present invention is further implemented by outputting lower current first and then adjusting higher and higher. Accordingly, the embodiment is implemented by the conductive circuit formed together by the current output unit (1), the first brushes (211), the conductive platform (3) and the pets (B) and the current output unit (1) can be enabled to control the value of the output current, which is gained from an initial first current value gradually to the predetermined current value.

Accordingly, when the embodiment is implemented, the user enables the current output unit (1) and grooms the pets (B) by using the comb body (2). The initial current value outputted by the current output unit (1) is shown in FIG. 8, which is outputted from the lower current value, the initial first current value, gradually to the current value satisfied with the predetermined current value (as shown in the figure but not limited to 5 A). Therefore, when the pets (B) are treated by the electrotherapy, they do not easily feel uncomfortable, and fear for the invention. Accordingly, the user treats the pets (B) by the physical therapy more easily.

Figure 9:
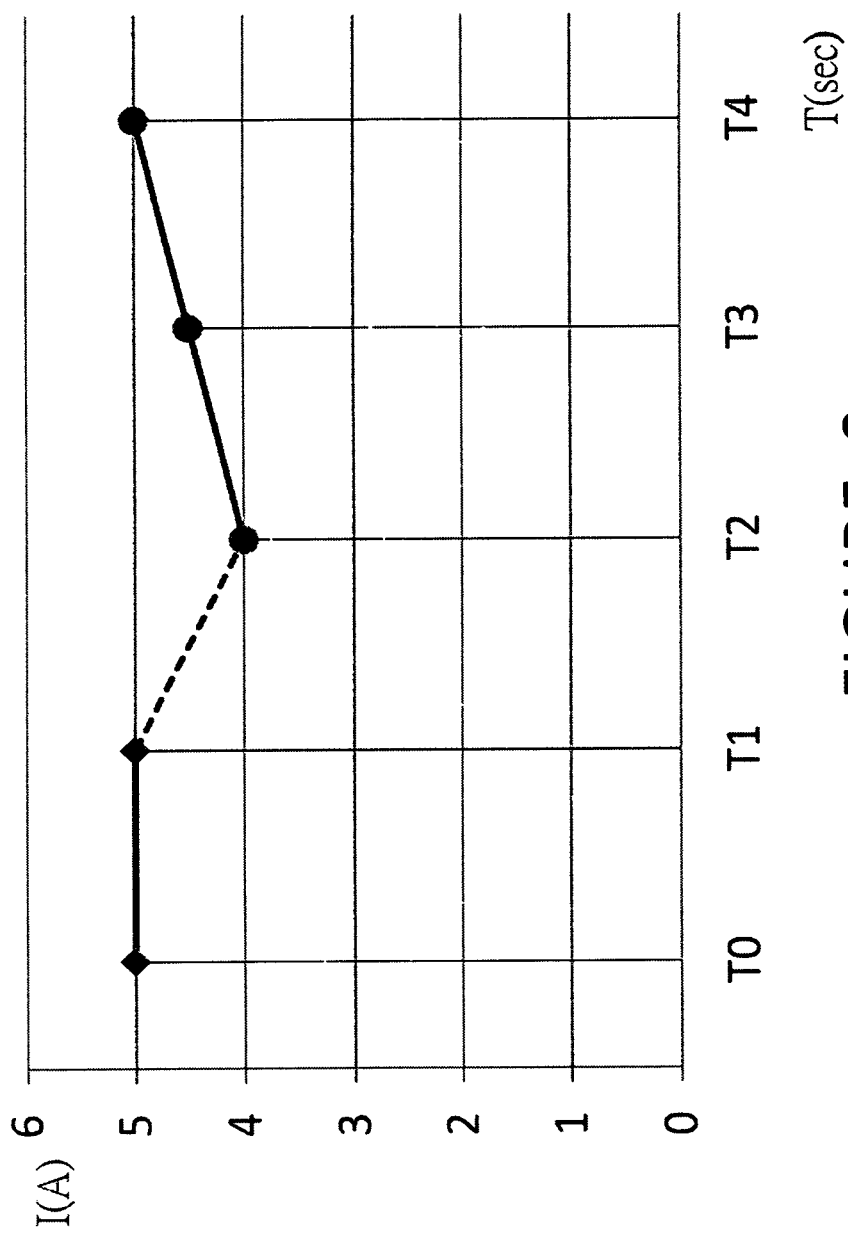
FIG. 9 illustrates the second schematic diagram of the output current of the current output unit of the present invention.

Referring to FIGS. 1 and 9, as the embodiments mentioned above, similarly, the pets (B) are treat by the electrotherapy but the treatment is temporarily interrupted and active again in the duration of the electrotherapy, the pets (B) still feel uncomfortable when the current output unit (1) continuously outputs the current by the predetermined current value. When the current output unit (1) decays the current to the initial first current value by the preceding state, it needs to wait for a time to treat the pets (B) via the predetermined current value by the electrotherapy. Therefore, the electrotherapy decay significantly.

Accordingly, as shown in FIGS. 7 and 9, the inventor attends to the problems. The embodiment is implemented as follows: determine the variation between the initial second current value and the predetermined current value to reduce the problems mention above according to the duration of the open circuit while the conductive circuit is temporarily at the state of the open circuit. Accordingly, the embodiment is implemented as follows: when the process of forming the conductive circuit by the current output unit (1), the first brushes (211), the conductive platform (3) and the pets (B) together is temporarily at a state of an open circuit, the current output unit (1) can be enabled to control the value of the output current from the initial second current value to the predetermined current value gradually and the variation between the initial second current value and the predetermined current value is proportioned to the duration of the open circuit.

Referring to FIGS. 7 and 9, in the duration of the physical therapy in the embodiment, if the comb body (2) departs from the surface of the body of the pets (B) so that the conductive circuit is an open circuit temporarily. Therefore, to avoid the conductive circuit being at the moment (as the dashed lines shown in the figure, which indicate the variations of the current schematic diagram from the open circuit to the short circuit) from the open circuit to the short circuit so that the pets (B) feel uncomfortable since the output current is interrupted, the current output unit (1) will output the current from the lower current value, the initial second current value (as shown in the figure but not limited to 4 A), gradually to the predetermined current value (as shown in the figure but not limited to 5 A) to reduce the whole uncomfortable feelings. Furthermore, the highest value of the initial second current value is a ninety percentage of the predetermined current value and the lowest value of the initial second current value is higher than the initial first current value to avoid the variations being to more or to less so that the whole effects of the physical therapy are affected.

In summary, the pets (B) lie on the conductive platform (3) and the comb body (2) is controlled to contact the skin of the pets (B) by the user. At the time, the current output unit (1) outputs the current continuously so that the current output unit (1), the first brushes (211), and the pets (F) form the conductive circuit together. In addition, to reduce the uncomfortable feelings of the pets (B), both the conductive silicone (2111) formed in the terminal of the first brushes (211) and the smart temperature controlling system is added to the physical therapy device for pets. During the grooming and the physical therapy, the temperature monitor unit (4) senses the temperature of the pets so as to heat or cool in that the pets (B), thus producing warm feelings (the hot pack) during the cold weather or the pets (B) gain the chill feelings such as the ice pack by the feedback of the temperature when they are injured and need the ice pack. The hot pack and the ice pack mentioned above can be set in the passive mode or can be sensed or set in the active mode.

In summary, the application conforms to the patent documents and is applied according to the patent acts. The descriptions mentioned above include the best embodiments in the invention but the scopes of the application base on the claims.

What is claimed is:

1. A physical therapy device for pets, comprising:
   a current output unit electrically connected to a power to supply an output current and control a current value of the output current;
   a comb body including a first terminal and a second terminal, wherein a side of the first terminal has multiple first brushes made of a plurality of conductive materials and separately electrically connected to the current output unit, and the second terminal is configured to be held by a user; and
   a conductive platform electrically connected to the current output unit so that the current output unit outputs the current to the pets via the multiple first brushes.

2. The physical therapy device for pets of claim 1, further comprising a temperature monitor unit electrically connected to the current output unit located inside the comb body, wherein the temperature monitor is configured to set a predetermined temperature value, a side of the first terminal has a second brushes made of a plurality of thermal conductive materials and separately connected to the temperature monitor unit and the temperature monitor unit maintains the second brushes at the predetermined temperature value.

3. The physical therapy device for pets of claim 2, wherein the temperature monitor unit is configured to senses a temperature in a peripheral environment and a temperature of the pets so as to determine the predetermined temperature value according to a result of sensing the temperature in the peripheral environment and the temperature of the pets.

4. The physical therapy device for pets of claim 3, further comprising a vibration unit that electrically connects connected to the current output unit arranged inside the second terminal, and a side of the second terminal has a plurality of bumps.

5. The physical therapy device for pets of claim 4, further comprising an odor releasing unit fixed inside the first terminal and configured to releases an odor, and a surface of the first terminal has a hole connected to the odor releasing unit.

6. The physical therapy device for pets of claim 5, further comprising a massage fork mounted in an end of the second terminal.

7. The physical therapy device for pets of claim 5, further comprising a massage member that includes clamps and mounted on a surface of the second terminal, which have an ability of a rebound to distant from each other under an external force or are close to each other under the force of the rebound, wherein inner portions in two terminals of the massage member separately have a wheel body.

8. The physical therapy device for pets of claim 6, further comprising a conductive silicone separately formed in a terminal of the first brushes.

9. The physical therapy device for pets of claim 8, wherein when the current output unit, the first brushes, the conductive platform, and the pets form the conductive circuit together, the current output unit controls the current value of the output current from an initial first current value gradually to a predetermined current value.

10. The physical therapy device for pets of claim 9, wherein when a process of forming the conductive circuit by the current output unit, the first brushes, the conductive platform and the pets together is temporarily at a state of an open circuit, the current output unit controls the current value of the output current from an initial second current value to the predetermined current value gradually and a variation between the initial second current value and the predetermined current value is proportioned to a duration of the open circuit.

11. The physical therapy device for pets of claim 9, wherein a highest value of the initial second current value is a ninety percentage of the predetermined current value and is higher than the initial first current value.

12. The physical therapy device for pets of claim 7, further comprising a conductive silicone separately formed in a terminal of the first brushes.

13. The physical therapy device for pets of claim 12, wherein when the current output unit, the first brushes, the conductive platform, and the pets form the conductive circuit together, the current output unit is enabled to controls the current value of the output current from an initial first current value gradually to a predetermined current value.

14. The physical therapy device for pets of claim 13, wherein when a process of forming the conductive circuit by the current output unit, the first brushes, the conductive platform and the pets together is temporarily at a state of an open circuit, the current output unit controls the current value of the output current from an initial second current value to the predetermined current value gradually and a variation between the initial second current value and the predetermined current value is proportioned to a duration of the open circuit.

15. The physical therapy device for pets of claim 14, wherein a highest value of the initial second current value is a ninety percentage of the predetermined current value and higher than the initial first current value.

16. The physical therapy device for pets of claim 1, wherein when the current output unit, the first brushes, the conductive platform, and the pets form the conductive circuit together, the current output unit controls the current value of the output current from an initial first current value gradually to a predetermined current value.

17. The physical therapy device for pets of claim 16, wherein when a process of forming the conductive circuit by the current output unit, the first brushes, the conductive platform and the pets together is temporarily at a state of an open circuit, the current output unit control the current value of the output current from an initial second current value to the predetermined current value gradually and a variation between the initial second current value and the predetermined current value is proportioned to a duration of the open circuit.

18. The physical therapy device for pets of claim 17, wherein a highest value of the initial second current value is a ninety percentage of the predetermined current value and is higher than the initial first current value.

19. The physical therapy device for pets of claim 18, further comprising a conductive silicone separately formed in a terminal of the first brushes.

20. The physical therapy device for pets of claim 19, further comprising a temperature monitor unit electrically connected to the current output unit mounted inside the comb body, wherein the temperature monitor is configured to set a predetermined temperature value, a side of the first terminal has multiple second brushes made of a plurality of thermal conductive materials and separately connected to the temperature monitor unit so that the temperature monitor unit maintains the second brushes at the predetermined temperature value.

* * * * *